United States Patent [19]

Kinet et al.

[11] Patent Number: 5,405,351
[45] Date of Patent: Apr. 11, 1995

[54] ENDOSCOPIC LOOP INCLUDING AN APPLYING INSTRUMENT

[75] Inventors: Jean-Pierre Kinet, Hensted-Ulzburg; Federico Bilotti, Hamburg; Pieter Brommersma, Norderstedt, all of Germany; Frederic Marie, Guise, France

[73] Assignee: Ethicon Endo-Surgery, Cincinnati, Ohio

[21] Appl. No.: 151,431

[22] Filed: Nov. 12, 1993

[30] Foreign Application Priority Data

Nov. 27, 1992 [DE] Germany .................. 42 40 533.5

[51] Int. Cl.$^6$ ............................................. A61B 17/04
[52] U.S. Cl. ......................... 606/139; 606/113; 606/144
[58] Field of Search .............. 606/113, 139, 144–148, 606/167, 170

[56] References Cited

U.S. PATENT DOCUMENTS 3,802,074 4/1974 Hoppe ............................ 30/134

FOREIGN PATENT DOCUMENTS 9100162.5 5/1991 Germany .............. A61B 17/04
9100162 9/1991 Germany .

Primary Examiner—Stephen C. Pellegrino
Assistant Examiner—Gary Jackson
Attorney, Agent, or Firm—Paul A. Coletti

[57] ABSTRACT

An endoscopic loop including an applying instrument comprises a pre-knotted loop of surgical suture material and a hollow shaft in the interior space of which the free thread portion runs. The free thread portion extends at least up to the proximal end of the shaft. In the interior space an actuating mechanism is mounted, the proximal end of which essentially extends up to the proximal end of the shaft. At the distal end of the actuating means a knife is attached which cuts the free thread portion upon actuation of the device.

7 Claims, 1 Drawing Sheet

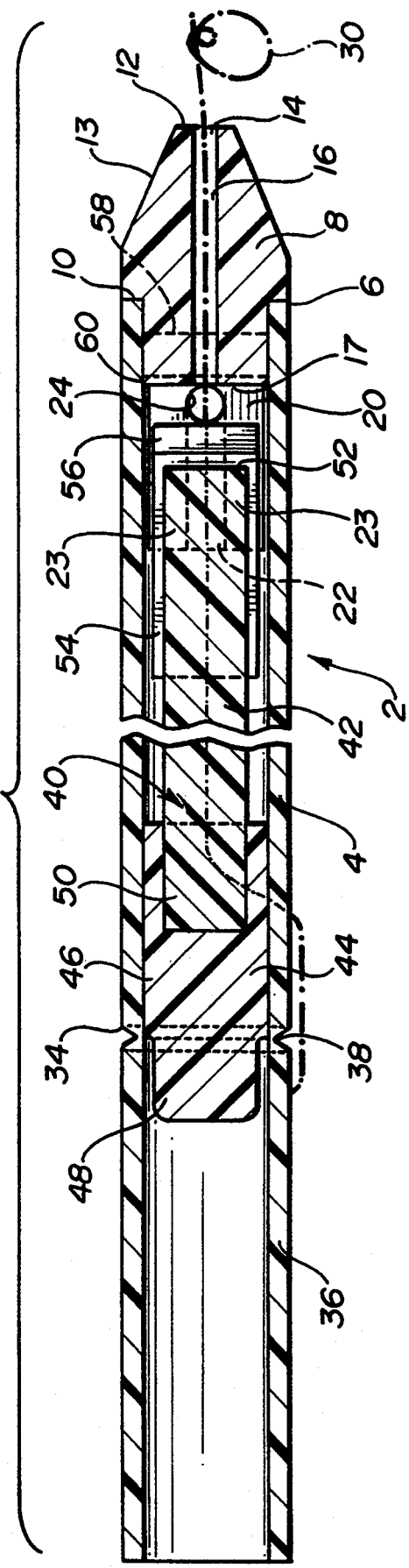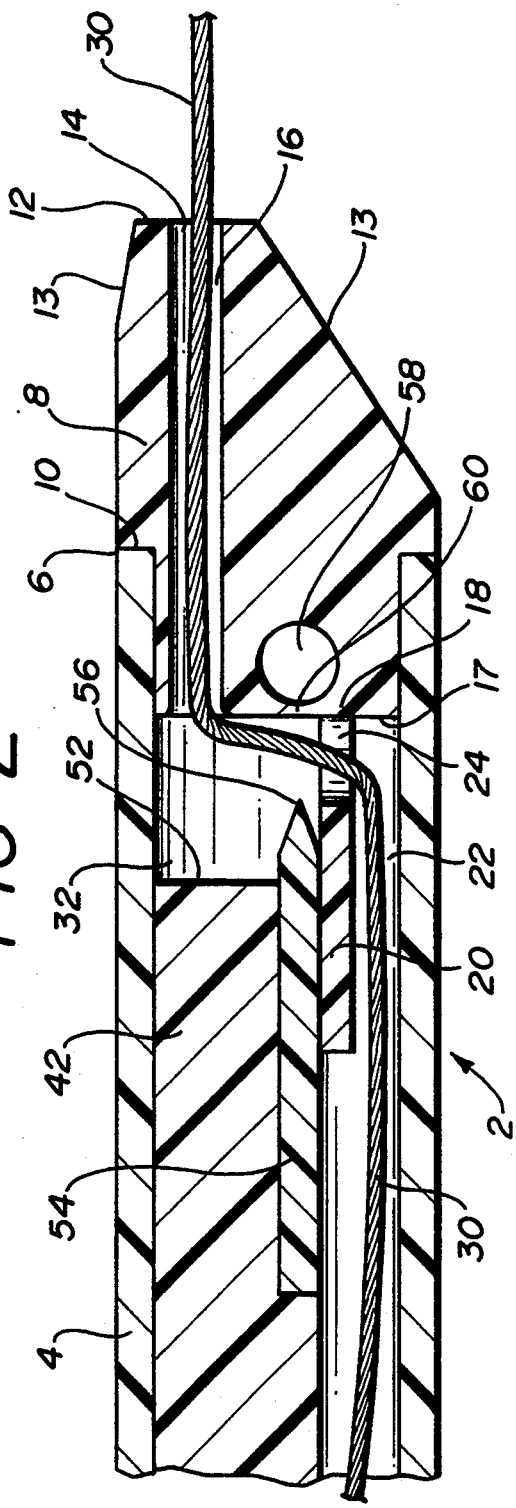

ENDOSCOPIC LOOP INCLUDING AN APPLYING INSTRUMENT

PRIORITY DATA

This application is based upon and claims priority from DE 4240533.5, filed Nov. 27, 1992, incorporated herein by reference.

BACKGROUND OF THE INVENTION

Pre-knotted loops for surgical purposes consist of suture material and have a slidable knot. They are used in order to ligate freely graspable stumps of a hollow organ or of a bundle of vessels. During endoscopic operations surgical instruments are introduced into the body through trocar sleeves. For such applications an endoscopic loop has proved useful. Such a loop comprises a suture thread formed into a loop having a slidable knot. The free thread portion is guided through an opening provided at the distal face of a thin hollow tube and extends in the interior space of the tube up to its proximal end. There, the loop is fixed to a cap or other kind of handle.

In order to apply the endoscopic loop, first it must be inserted into an auxiliary sleeve which covers the folded loop (including the knot) at its distal portion. After introducing the auxiliary sleeve through the trocar into the abdominal cavity, the auxiliary sleeve is retracted so that the loop becomes accessible. An endoscopic forceps grasps the loop and lays it about the stump. Afterwards the loop is pulled tight by moving the cap or handle in the proximal direction. During this procedure the knot abuts the opening in the distal face of the tube. Finally, the free thread portion is cut using a cutting instrument introduced through another trocar sleeve.

A disadvantage in the application of the known endoscopic loop is that the cutting step is time consuming. Moreover, the surgeon has to be very careful in order to cut just the thread and not to hurt the patient.

SUMMARY OF THE INVENTION

It is an object of the present invention to provide an endoscopic loop including an applying instrument which enables a fast and safe application.

The endoscopic loop including an applying instrument according to the present invention comprises a pre-knotted loop of suture material, the free thread portion of which enters the interior space of a hollow shaft through an opening provided at the distal end portion of the shaft. This opening cannot enclose the knot. In the interior space a longitudinally shiftable actuating means is supported. At its distal end a cutting means is attached. The cutting means is able to cut the free suture portion when the actuating means is moved in the distal direction.

In order to apply the endoscopic loop according to the present invention, first the instrument including the loop is covered by an auxiliary sleeve and inserted through a trocar sleeve, similar to a conventional endoscopic loop instrument. After retracting the auxiliary sleeve and after laying the loop around the organ stump, the loop (which extends at least up to the proximal end of the shaft), is pulled tight by drawing (in the proximal direction) the free thread portion. Finally, the actuating means is pressed which causes the cutting means to move toward the free suture thread portion and cut it. In this way, the free thread portion is separated from the loop at a position having a predetermined distance from the knot. The cutting procedure is quick and safe, because the cutting means is encapsulated in the hollow shaft.

In a preferred embodiment the proximal end of the actuating means is covered by a safety cap. Preferably the safety cap is connected to the proximal end of the shaft via a frangible line. The end of the free thread portion can be fixed at the safety cap. The safety cap prevents unintentional actuation of the instrument. In order to tighten the loop, the surgeon moves the safety cap in order to separate it from the shaft along the frangible line. Afterwards, the surgeon uses the safety cap as a handle to pull the free thread portion. Finally, the actuating means is operated to cut the thread.

In a preferred embodiment, the free suture thread portion is guided between a support and the cutting edge of the cutting means so that it traverses the cutting edge. The support serves as an anvil and is provided with a cavity which is positioned opposite to the cutting edge. When the instrument is actuated, the cutting edge first penetrates the thread and afterwards the thin wall between the surface of the support and the cavity. In this way, the surgeon receives a feedback signal; after the cutting edge has penetrated the wall, the actuating means moves more easily in the distal direction by a distance corresponding to the thickness of the cavity. Without getting such a feedback signal, the surgeon would not be absolutely sure if the thread had been cut.

DESCRIPTION OF THE DRAWINGS

In the following the present invention is explained in more detail by means of an embodiment. The drawings show:

FIG. 1 is a longitudinal section of an instrument according to the present invention from which the preknotted loop including the free thread portion has been removed; in the distal region, the view of several parallel sectional planes are superimposed on each other; and FIG. 2 is a longitudinal section of the instrument according to FIG. 1 along the center plane extending perpendicular to the sectional planes of FIG. 1.

DETAILED DESCRIPTION OF THE INVENTION

As shown in FIG. 1 and in FIG. 2, the instrument according to the present invention includes a hollow shaft 2. The shaft 2 comprises a preferably cylindrical shaft tube 4 having a distal end 6 and a head piece 8. The head piece 8 is provided with an annular recess forming an abutting surface 10 which rests against the distal end 6 of the shaft tube 4 when the head piece 8 is fixed to the shaft tube 4.

The distal face 12 of the head piece 8 has an opening 14 which forms the distal end of a channel 16, connecting the distal face 12 with the proximal face 17 of the head piece 8. The region of the head piece 8 close to its proximal face 17 forms a support 18 which will be explained later.

Preferably, the side regions 13 of the head piece 8 are tapered as shown.

Inside the shaft tube 4 and close to the head piece 8, a guide piece 20 is mounted; guide piece 20 forms a guiding zone 22 between one of its surfaces and the opposing inner surface of the shaft tube 4. As shown in FIG. 1, the guide piece 20 is attached to the shaft tube 4 via two side portions 23. At the distal end of the guide piece 20 is provided an opening 24.

The instrument according to the present invention comprises a pre-knotted loop made of a suture thread suitable for surgical purposes. The loop is formed in a well-known manner by knotting one of the thread ends to the middle region of the thread. The knot applied is a slidable knot (or slip knot). The free suture thread portion is fed through the opening 14 into the interior space 32 of the shaft 2, as shown in FIG. 2. When the instrument according to the present invention is ready for use, e.g., after it has been unwrapped from a sterile package, the knot preferably touches the distal face 12 of the head piece 8. The diameter of opening 14 is small enough to prevent the knot from entering into the channel 16.

While FIG. 2 does not display the complete loop including the knot, it indicates the way how the free thread portion 30 is guided in the interior space 32 of shaft 2. When leaving the channel 16 the free thread portion 30 curves and runs essentially parallel to the support 18 until it passes the opening 24, where it curves again and is channeled through the guiding zone 22. In the middle and proximal region of shaft 2, the free thread portion 30 runs essentially parallel to the longitudinal axis and close to the wall of the shaft tube 4. Preferably, the edges coming into contact with the free thread portion 30 are rounded.

In the embodiment described a safety cap 36 is attached to the proximal end 34 of shaft tube 4, see FIG. 1. Here the safety cap 36 has the shape of a hollow cylinder open at both sides. Preferably the safety cap 36 and the shaft tube 4 are made as one piece, and at the proximal end of shaft tube 4 an annular notch 38 is provided which forms a breaking line. In this way, pressing the safety cap 36 in a direction (essentially perpendicular to the longitudinal axis of shaft 2) causes the material at notch 38 to break, so that the safety cap 36 can be separated from the shaft tube 4.

Preferably, the proximal end of the free suture thread portion 30 (not shown in FIG. 1) is fixed to the safety cap 36. Thus, safety cap 36 can serve as a handle for pulling the free thread portion 30 when the safety cap 36 is moved in the proximal direction with respect to shaft tube 4. In this way, the loop is tightened provided that the knot abuts against the distal face 12.

In the interior space 32 of shaft tube 4, an actuating means 40 is guided in a longitudinally movable manner. The actuating means 40 comprises an actuating rod 42 in its distal region and an actuating button 44 close to its proximal end. The distal region 46 of actuating button 44 is cylindrically shaped with an outer diameter corresponding to the internal diameter of shaft tube 4. The proximal region 48 of actuating button 44 extends beyond the proximal end 34 of shaft tube 4. It is covered by the safety cap 36 before the instrument is used. The safety cap 36 can be easily separated without unintentionally operating the actuating button 44. On one side of actuating button 44 a channel for passing the free thread portion 30 is provided (not shown in FIG. 1). The proximal region 50 of the actuating rod 42 is inserted into a bore in the actuating button 44, see FIG. 1.

Close to the distal end 52 of the actuating rod 42 is held a knife 54, maintained in a recess provided on one longitudinal side of the actuating rod 42, see FIG. 2. The knife 54 is fixed, e.g., by means of a rivet. At its distal end, the knife 54 has a cutting edge 56 which extends essentially perpendicular to the longitudinal axis of shaft 2, and thereby traverses the region of the free suture thread portion 30 which runs along the support 18.

While the proximal region 50 of the actuating rod 42 is guided via the actuating button 44, the region close to the distal end 52 is supported by the guide piece 20, which abuts against knife 54, as shown in FIG. 2. Before the instrument is used, the cutting edge 56 of knife 54 is held proximally away from the support 18, see FIG. 2. The actuating means 40 including the knife 54 is kept in this state by friction or other appropriate means.

Alternatively, the knife could be held in its initial position by means of a spring which is stressed upon actuation. Another possibility for keeping the initial distance between the cutting edge and the support is for example a rigid connection between the actuating means and the shaft via a weak frangible line, which is destroyed when the instrument is actuated in order to cut the free thread portion.

Opposite the cutting edge 56, the support 18 is provided with a cavity 58 which preferably is a cylindrical bore running in parallel to the cutting edge 56 and extending over the whole width thereof, as displayed in FIG. 1 and 2. The wall 60 between the proximal face 17 of head piece 8 and the interior surface of cavity 58 is thick enough to form a safe support or anvil during the cutting procedure of the free thread portions 30, but thin enough to be easily penetrable by the cutting edge 56 as long as the pressure force exerted on the actuating button 44 is high enough.

The instrument according to the embodiment of FIG. 1 and FIG. 2 is applied in the following way. Before use, the safety cap 36 is in place and precludes an unintentional actuation of actuating button 44. In this state, the knot preferably abuts against the distal face 12, but it can be shifted in the distal direction in order to reduce the size of the loop if desired. During an endoscopic operation the loop including the instrument is inserted into a body cavity through a trocar sleeve, employing an auxiliary sleeve as described before, and the loop is laid about an organ stump. In order to tighten the loop, the surgeon presses the safety cap 36 sidewardly with respect to shaft tube 4, thus separating it from shaft 2 along the breaking line. Afterwards the safety cap 36 is pulled away from shaft 2, thus tightening the loop. Finally, the actuating button 44 is pressed until the free thread portion 30 is cut. Further pressure onto the actuating button 44 causes cutting edge 56 to penetrate the wall 60. Then, the cavity 58 is unable to exert a reaction force causing the actuating means 40 to suddenly move in distal direction by a distance corresponding to the diameter of the cavity 58. This gives the surgeon a signal that the free suture thread portion 30 has been cut. The length of channel 16 defines the length of a remaining thread portion which is necessary to prevent the loop from loosening. The part of the free thread portion 30 which has been cut remains in the instrument. Thus it is safely removed from the body cavity by retracting the instrument.

The design of the embodiment displayed in FIGS. 1 and 2 allows low cost manufacturing of the endoscopic loop instrument (e.g. essentially from a suitable plastic material) so that it can be used as a disposable product. Alternatively, the applying instrument can be designed to be reusable. In this case, after each use, the instrument has to be sterilized and the free thread portion of a fresh loop has to be inserted.

While the application field of the present invention is preferably that of endoscopic operations, it is imaginable to employ its advantages also in open surgery.

We claim:

1. Endoscopic loop and applying instrument, comprising:
    a pre-knotted loop of surgical suture material having a free suture thread portion; and an instrument having a hollow shaft with proximal and distal ends and having a longitudinal axis, the suture material emplaced in said hollow shaft;
    the free suture thread portion of said loop entering said hollow shaft through an opening provided in the distal end of said shaft, said free suture thread portion extending up toward the proximal end of said shaft;
    a longitudinally shiftable actuating means mounted in said shaft, the proximal end of said actuating means essentially extending up to the proximal end of said shaft; and
    a knife attached to the distal end of said actuating means, said knife having a cutting edge adapted to cut said free suture thread portion.

2. The instrument according to claim 1, characterized in that the proximal end of said actuating means is shaped as an actuating button and protrudes from the proximal end of said shaft.

3. The instrument according to claim 2, characterized in that the proximal end of said actuating means is covered by a safety cap.

4. The applying instrument according to claim 3, characterized in that before use said safety cap is connected to the proximal end of said shaft at a frangible section.

5. The instrument according to claim 3, characterized in that the end of said free suture thread portion is fixed at said safety cap.

6. The instrument according to claim 1, characterized in that the cutting edge of said knife extends essentially parallel to the longitudinal axis of said shaft.

7. The instrument according to claim 6, characterized in that said free suture thread portion is guided in the distal end of said shaft between a support and a channel extending essentially parallel to the longitudinal axis of said shaft.

* * * * *